(12) United States Patent
Barrette et al.

(10) Patent No.: US 6,197,031 B1
(45) Date of Patent: Mar. 6, 2001

(54) THREADED DRILL/IM ROD

(75) Inventors: John J. Barrette, Warsaw; Adam Griner, Columbia City; Richard A. Lane, Fort Wayne, all of IN (US)

(73) Assignee: Bristol-Myers Squibb Co., New York, NY (US)

( * ) Notice: Subject to any disclaimer, the term of this patent is extended or adjusted under 35 U.S.C. 154(b) by 0 days.

(21) Appl. No.: 09/392,040

(22) Filed: Sep. 8, 1999

(51) Int. Cl.[7] .................................................. A61B 17/00
(52) U.S. Cl. .................................. 606/80; 606/72; 606/73
(58) Field of Search .................................. 606/80, 88, 86, 606/87, 89, 62, 79, 96

(56) References Cited

U.S. PATENT DOCUMENTS

| | | | |
|---|---|---|---|
| 4,463,753 | * | 8/1984 | Gustilo ..................................... 606/80 |
| 4,710,075 | * | 12/1987 | Davison .................................. 606/80 |
| 4,830,000 | * | 5/1989 | Shutt ....................................... 606/80 |
| 4,978,350 | * | 12/1990 | Wagenknecht .......................... 606/72 |
| 5,573,537 | * | 11/1996 | Rogozinski ............................. 606/80 |
| 5,613,970 | | 3/1997 | Houston et al. ......................... 606/88 |
| 5,908,423 | * | 6/1999 | Kashuba et al. ........................ 606/80 |
| 5,941,706 | * | 8/1999 | Ura ......................................... 606/80 |

OTHER PUBLICATIONS

NexGen Complete Knee Solution Tibial Stem Extension & Augmentation Surgical Technique; 97–5988–102; 1996 Zimmer, Inc.

Miller/Galante Total Knee System Technique; 97–5780–02; Rev 2 1985, 1988 Zimmer, Inc.

* cited by examiner

*Primary Examiner*—Pedro Philogene
(74) *Attorney, Agent, or Firm*—Cary R. Reeves

(57) ABSTRACT

An IM rod has a proximal threaded portion that threads into the bone to increase the stability of the rod. The rod further includes an extended pointed tip for positive slip-free placement of the rod on the bone and an end cutting drill and reaming flutes for drilling a hole into and reaming the IM canal. Conformity between the shaft and the IM canal is increased to maximize stability by including a starter tip and drill as integral extensions of the shaft. Flutes extend up the rod beyond the drilling and reaming portion to allow decompression of the IM canal as the rod is inserted into the canal.

16 Claims, 3 Drawing Sheets

THREADED DRILL/IM ROD

BACKGROUND OF THE INVENTION

The present invention relates to intramedullary rods for use in conjunction with instruments for orthopaedic surgery.

A common technique for resecting the ends of bones during orthopaedic surgery involves the use of an intramedullary (IM) rod to provide a reference to the axis of the bone and to provide a support base for measurement and resection instruments. An example of such a prior art technique and instruments is found in the *Miller/Galante Total Knee System Surgical Technique* published and sold by Zimmer, Inc. In this system, a starter instrument is used to form a small indentation or hole in the end of the bone. A drill is then used to enlarge the starter hole and drill into the IM canal. Alignment guides and other instruments having an IM rod are then inserted into the canal. An improvement in IM instrument technique is taught in U.S. Pat. No. 5,613,970 assigned to Zimmer, Inc., and in the *NexGen®Complete Knee Solution Tibial Stem Extension & Augmentation Surgical Technique* published by Zimmer, Inc. The improvement is the use of an IM reamer that is left in place after the IM canal is reamed and on which various instruments can be mounted. This improvement saves the steps of removing the drill or reamer and inserting a separate IM rod.

SUMMARY OF THE INVENTION

The present invention improves on the prior art IM instruments and techniques by providing an IM rod having a proximal threaded portion that threads into the bone to increase the stability of the rod. The rod further includes an extended, pointed tip for positive slip-free placement of the rod on the bone and an end cutting drill and reaming flutes for drilling a hole into and reaming the IM canal. Conformity between the shaft and the IM canal is increased to maximize stability by including a starter tip and drill as integral extensions of the shaft. Flutes extend up the rod beyond the drilling and reaming portion to allow decompression of the IM canal as the rod is inserted into the canal.

DETAILED DESCRIPTION OF THE INVENTION

Figure 1:
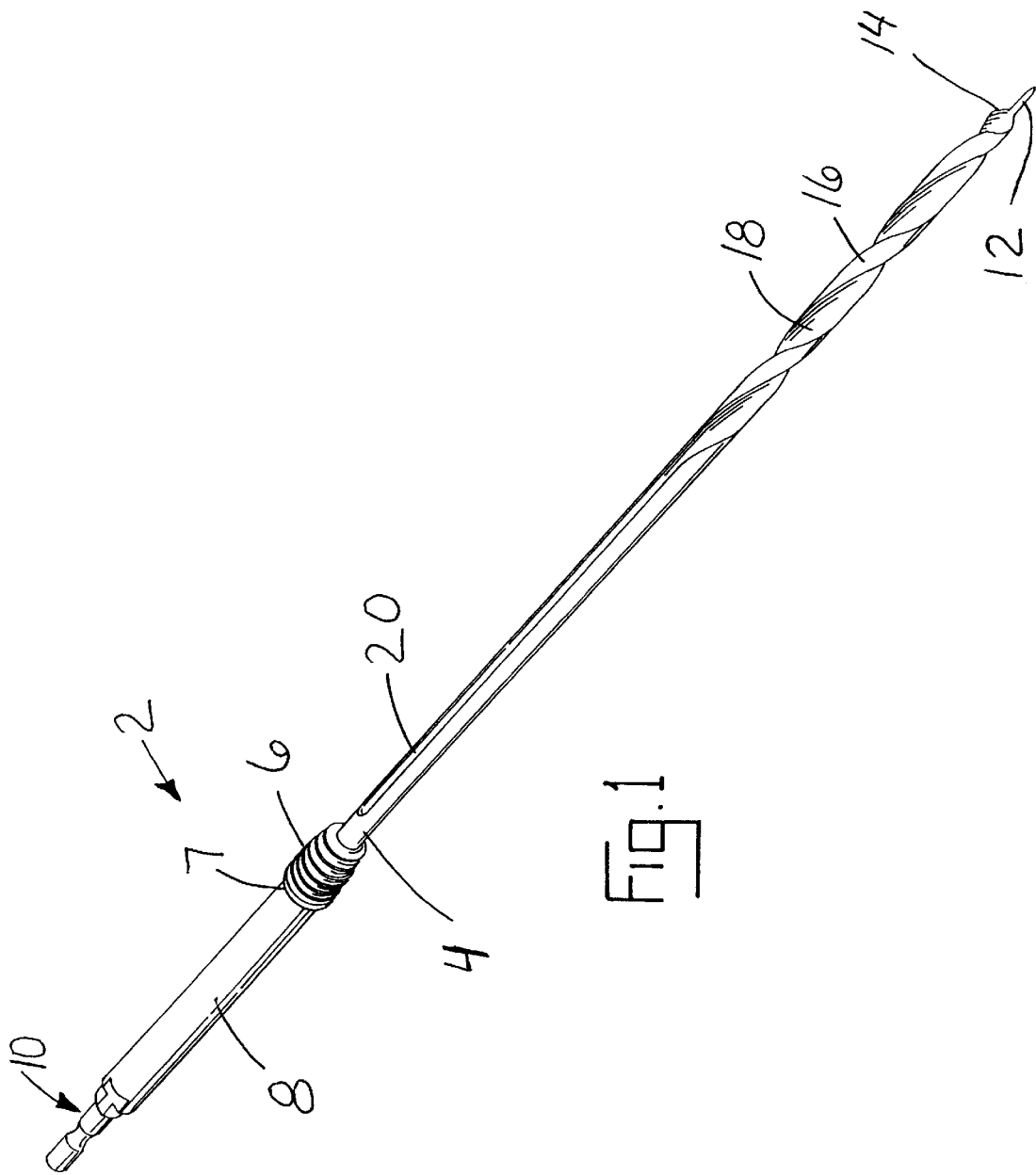
FIG. 1 is a perspective view of an IM rod according to the present invention.
Figure 2:
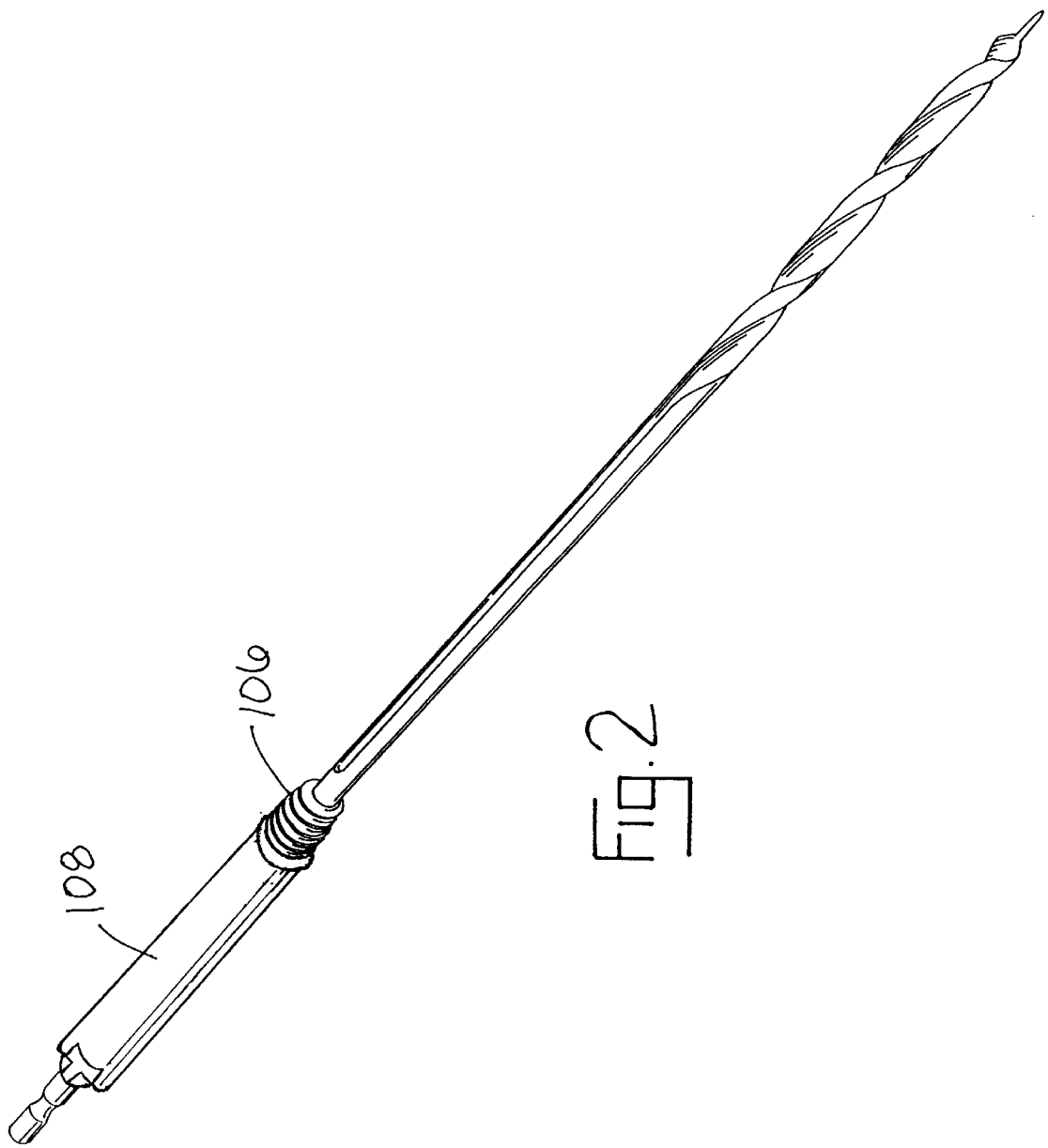
FIG. 2 is a perspective view of an alternative embodiment of an IM rod according to the present invention.
Figure 3:
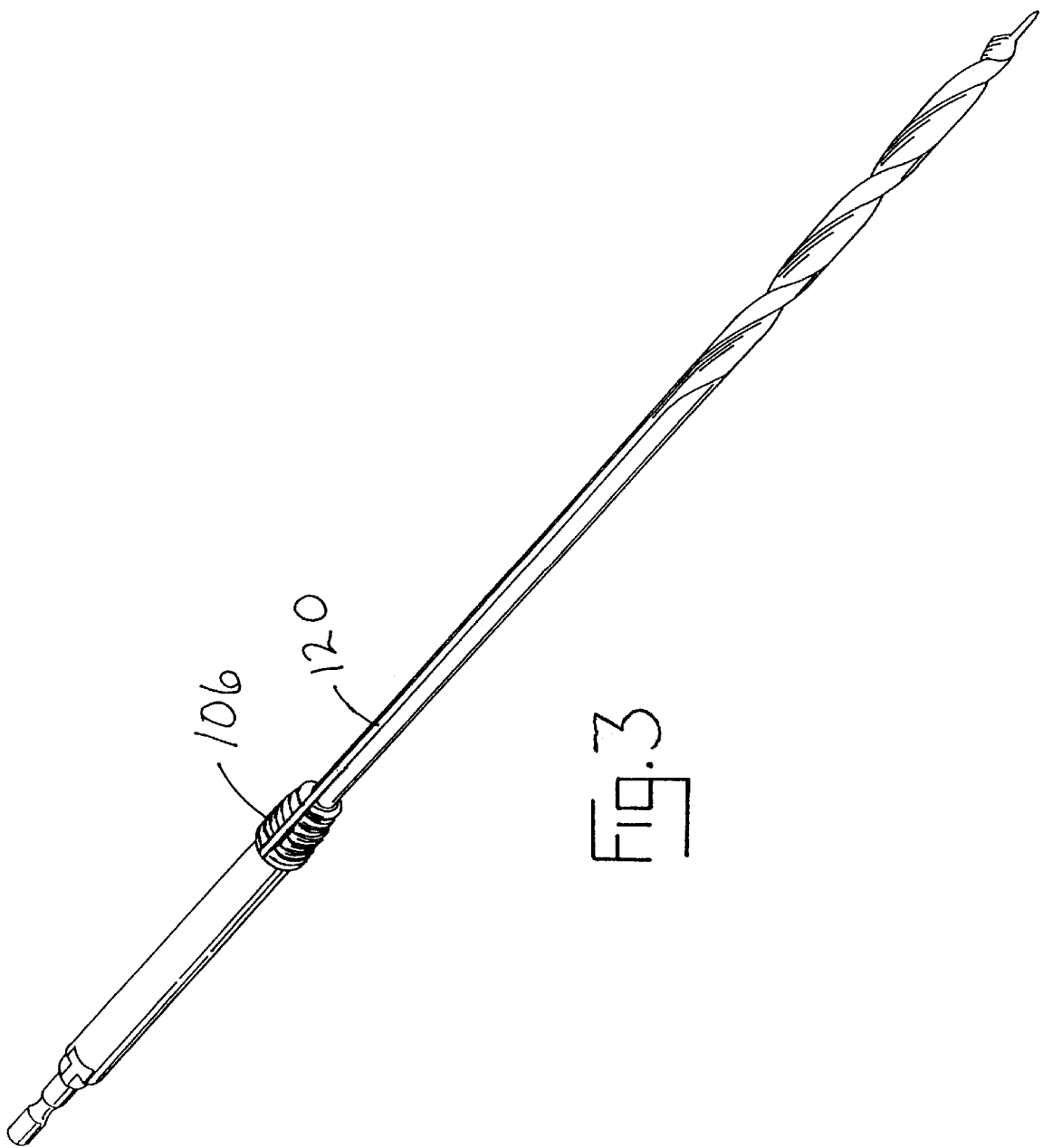
FIG. 3 is a perspective view of an alternative embodiment of an IM rod according to the present invention.

FIG. 1 depicts an IM rod 2 according to the present invention. The rod 2 includes a shaft 4 for insertion into the IM canal of a long bone such as a tibia or femur. A screw thread 6 is formed at the proximal end of the shaft 4. When the IM rod 2 is inserted into an IM canal, the screw thread can be screwed into the proximal end of the canal to stabilize the rod 2 and prevent longitudinal pistoning, rotation, and side-to-side motion of the rod. This increased stability leads to more accurate measurement and cutting with instruments mounted on the rod 2. The screw thread in the exemplary embodiment is smooth and tapered. However, the thread can alternatively have a cutting flute so that it is self-tapping, as shown in the embodiment of FIG. 3, to facilitate its threading into the cortical bone typically found at the ends of long bones. A mounting shank 8 extends proximally from the threaded portion of the shaft 4. The mounting shank 8 is preferably a smooth cylinder on which measurement and resection instruments can be mounted. The mounting shank 8 has a diameter smaller than the screw thread 6, as shown, to form a shoulder 7 for seating an instrument. A driver end 10 extends proximally from the mounting shank 8. The driver end 10 preferably includes features for positive engagement with a driver such as are provided by the Zimmer standard adapter In an alternative embodiment shown in FIG. 2, the shank 108 can have a diameter larger than the screw thread 106. In this alternative embodiment, an instrument can be clamped to the shank 108 for alignment purposes and then the instrument can be attached to the bone such as with pins or screws. Since the thread 106 is smaller than the shank 108, it can be withdrawn through the instrument leaving the instrument in place.

The distal end of the shaft 4 is preferably provided with features to facilitate rapid and accurate insertion of the shaft into the IM canal. A starter tip 12 projects from the distal end of the shaft 4. The starter tip 12 comprises a smooth cylindrical or conical extension sharpened at its free end. Preferably the tip 12 extends two or more millimeters. An end cutting drill 14 is behind the tip 12. The drill 14 includes helical lands 16 and flutes 18. The lands 16 guide the drill 14 along the IM canal and the flutes 18 transport cut material away from the end of the drill. The lands 16 can optionally be sharpened so that they ream the sides of the canal. Straight flutes 20 continue from the helical flutes 18 along the shaft 4 toward the proximal end of the shaft 4. Preferably the straight flutes 20 extend to the threads 6. In the alternative embodiment shown in FIG. 3, the flutes 120 extend through the 206 threads. In the embodiment where the threads are self-tapping, the straight flutes 120 advantageously form the tapping flutes.

In use, the starter tip 12 is placed on the end of a bone in alignment with the IM canal. An impact force on the rod 2, or a pushing twisting motion, causes the tip 12 to bite into the bone. Because the tip is extended, it can penetrate into the bone as much as a few millimeters to prevent any slipping or "walking" of the drill. Next the rod 2 is turned to drill into the end of the bone and into the IM canal. Since the straight flutes 20 continue from the helical flutes 18, there is no obstacle to the flow of material up the shaft 4. As the rod is inserted into the canal, the flutes 18 and 20 provide a place for the bone marrow and other canal materials to flow thus preventing injury due to compression of these materials. The rod 2 is drilled into the canal until the threads 6 contact bone. The threads 6 are turned into the bone to provide positive engagement and stabilization of the rod 2. Measurement, resection, and other instruments can then be mounted on the shank 8 for resecting the bone end as is known in the art. Stability is enhanced in the present invention by including a starter tip and drill as integral extensions of the shaft. This combination eliminates multiple instrument insertions and removals and eliminates size mismatches between sequential instruments both of which can cause poor fit between the canal and rod 2. With the integral tip and drill, the drill and rod size relationship can be more easily and closely controlled since they are machined as a single piece. These improvements increase the speed of the operation, decrease the number of instruments required, and increase the conformity between the shaft 4 and the IM canal to maximize stability.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A rod for insertion into the intramedullary canal of a human bone to provide an instrument mounting base, the rod comprising:
   a shaft having a first end and a second end;
   a screw thread formed near the first end;
   an instrument mounting shank extending outwardly from the first end away from the screw thread;
   a helical drilling portion having at least one land and at least one flute on the second end of the shaft; and
      at least one straight flute extending from the at least one drilling flute, the straight flute extending along the shaft toward the screw thread and ending near the screw thread.

2. The rod of claim 1 wherein the screw thread has a major diameter that is greater than a major diameter of the shaft.

3. The rod of claim 1 wherein the screw thread has a major diameter that is less than a major diameter of the mounting shank.

4. The rod of claim 1 further comprising a sharpened tip extending from the second end of the shaft.

5. The rod of claim 4 wherein the tip has a smooth outer surface extending at least 2 millimeters from the second end of the shaft and wherein the free end of the tip comes to a point.

6. The rod of claim 1 wherein the at least one straight flute extends at least part way into the screw thread.

7. The rod of claim 1 further comprising a positive engagement driver end adjacent the shank.

8. The rod of claim 6 further comprising a positive engagement driver end adjacent the shank.

9. A rod for insertion into the intramedullary canal of a human bone to provide an instrument mounting base, the rod comprising:
   a shaft having a first end and a second end;
   an instrument mounting shank extending outwardly from the first end of the shaft;
   a sharpened tip extending from the second end of the shaft;
   a helical drilling portion having at least one land and at least one flute on the second end of the shaft located above the tip;
   a screw thread formed near the first end; and
   at least one straight flute extending from the at least one drilling flute, the straight flute extending along the shaft toward the screw thread and ending near the screw thread.

10. The rod of claim 9 further comprising a positive engagement driver end adjacent the shank.

11. The rod of claim 9 wherein the at least one flute extends at least part way into the screw thread.

12. A rod for insertion into the intramedullary canal of a human bone to provide an instrument mounting base, the rod comprising:
   a shaft having a first end and a second end;
   a screw thread formed near the first end;
   an instrument mounting shank extending outwardly from the first end away from the screw thread;
   a helical drilling portion having at least one land and at least one drilling flute on the second end of the shaft;
   at least one straight flute extending from the at least one drilling flute, the at least one straight flute extending along the shaft toward and at least part way into the screw thread;
   wherein the screw thread has a major diameter that is greater than a major diameter of the shaft;
   wherein the screw thread has a major diameter that is less than a major diameter of the mounting shank;
   a sharpened tip extending from the second end of the shaft and having a smooth outer surface extending at least two millimeters from the second end of the shaft and wherein the free end of the tip comes to a point; and
   a positive engagement driver end adjacent the shank.

13. A method of inserting a rod into the intradmedullary canal of a human bone to provide an instrument mounting base, comprising:
   providing an intramedullary rod having a distal insertion end, a proximal tool mounting end, a screw thread formed near the proximal tool mounting end, and an instrument mounting shank extending outwardly and away from the screw thread toward the proximal tool mounting end;
   placing the distal insertion end in abutting relationship with the end of the human bone;
   inserting the intramedullary rod into the intramedullary canal of the human bone until the screw thread abuts the end of the bone; and
   turning the rod to engage the screw thread with the bone and thereby stabilize the rod.

14. The method of claim 13, wherein said intramedullary rod further comprises a helical drilling portion having at least one land and at least one flute on the distal insertion end of the rod, and at least one straight flute extending from the at least one drilling flute, the straight flute extending along the shaft toward the screw thread and ending near the screw thread, and wherein said method of inserting a rod into the intramedullary canal of a human bone comprises drilling the intramedullary rod into the intramedullary canal of the human bone.

15. A method of inserting an intramedullary rod into the intramedullary canal of a human bone to provide an instrument mounting base, comprising:
   providing an intramedullary rod having: a distal insertion end with a sharpened tip extending therefrom, a helical drilling portion having at least one land and at least one flute on the distal insertion end of the rod located above the tip, an intermediate shaft having at least one straight flute extending from the at least one drilling flute, the straight flute extending along the shaft toward a screw thread, said screw thread formed near a proximal tool mounting end of the intramedullary rod;
   probing an end of the bone with the sharpened tip of the intramedullary rod;
   driving the tip of the intramedullary rod into the bone end;
   turning the intramedullary rod to actuate the helical drilling portion of the intradmedullary rod and drill a hole into the intramedullary canal of the bone until the screw thread of the intramedullary rod abuts the end of the bone; and
   further turning the intramedullary rod to engage the thread thereof with the bone and stabilize the rod.

16. The method of claim 15, wherein the at least one straight flute of the intramedullary rod extends at least part way into the screw thread of the intramedullary rod.

* * * * *